(12) United States Patent
Gray et al.

(10) Patent No.: US 9,034,302 B2
(45) Date of Patent: May 19, 2015

(54) MINERAL SUNSCREEN COMPOSITION AND PROCESS FOR PROTECTING SKIN FROM PHOTODAMAGE AND AGING

(75) Inventors: Timothy Gray, New York, NY (US); Paula Cziryak, Eatontown, NJ (US); Ana Kljuic, New York, NY (US)

(73) Assignee: L'OREAL, Paris (FR)

( * ) Notice: Subject to any disclaimer, the term of this patent is extended or adjusted under 35 U.S.C. 154(b) by 440 days.

(21) Appl. No.: 13/084,085

(22) Filed: Apr. 11, 2011

(65) Prior Publication Data
US 2012/0258055 A1   Oct. 11, 2012

(51) Int. Cl.
| | |
|---|---|
| A61K 8/00 | (2006.01) |
| A61K 8/26 | (2006.01) |
| A61Q 17/04 | (2006.01) |
| A61K 8/25 | (2006.01) |
| A61K 8/19 | (2006.01) |

(52) U.S. Cl.
CPC . *A61K 8/26* (2013.01); *A61Q 17/04* (2013.01); *A61K 8/25* (2013.01); *A61K 8/19* (2013.01)

(58) Field of Classification Search
CPC ............. A61K 8/19; A61K 8/25; A61K 8/26; A61K 8/35; A61Q 17/04
USPC .......................................................... 424/59
See application file for complete search history.

(56) References Cited

U.S. PATENT DOCUMENTS

| | | | |
|---|---|---|---|
| 5,143,722 A | 9/1992 | Hollenberg | |
| 5,665,368 A | 9/1997 | Lentini | |
| 5,958,431 A | 9/1999 | Brancq et al. | |
| 7,204,975 B2* | 4/2007 | Wendel et al. | 424/59 |
| 2007/0178057 A1* | 8/2007 | SenGupta et al. | 424/59 |
| 2007/0292530 A1 | 12/2007 | Dinno | |
| 2008/0220065 A1* | 9/2008 | Gelvin | 424/486 |
| 2008/0269352 A1 | 10/2008 | Falkoswki et al. | |
| 2009/0324506 A1 | 12/2009 | Seidling | |
| 2010/0183536 A1 | 7/2010 | Ansmann et al. | |

FOREIGN PATENT DOCUMENTS

| | | |
|---|---|---|
| EP | 1174119 | 1/2002 |
| WO | WO 92/06778 | 4/1992 |
| WO | WO 2006-013413 | 2/2006 |
| WO | WO 2007-068371 | 6/2007 |
| WO | WO 2008-155059 | 12/2008 |

* cited by examiner

*Primary Examiner* — Aradhana Sasan
(74) *Attorney, Agent, or Firm* — McNees, Wallace & Nurick, LLC (57) ABSTRACT

The present invention is directed to a composition and method for protecting a keratinous substrate from harmful UV rays by applying onto the substrate a composition containing: (a) at least one oil phase thickening agent chosen from an activated clay; (b) at least one substantially solid form dispersing aid; (c) at least one non-volatile solvent; (d) at least one inorganic sunscreen active; (e) at least one emulsifier; (f) at least one volatile solvent; and (g) water, and wherein (a) and (b) are present in the composition in a ratio by weight ranging from greater than 1:4 to less than 1:10.

22 Claims, 1 Drawing Sheet

US 9,034,302 B2

MINERAL SUNSCREEN COMPOSITION AND PROCESS FOR PROTECTING SKIN FROM PHOTODAMAGE AND AGING

FIELD OF THE INVENTION

The present invention is directed to a novel mineral sunscreen composition and process for protecting skin from photodamage, the composition having exceptional skin-feel properties with highly efficacious spreadability and non-whitening application. More particularly, the invention is directed to a mineral sunscreen composition containing activated clay combined with a dispersing aid/agent and one or more inorganic sunscreen active, wherein the clay and dispersing aid synergistically mitigate re-agglomeration of the inorganic sunscreen active, thereby resulting in a mineral sunscreen having high UVB/UVA protection and exceptional spreadability that is non-whitening.

BACKGROUND OF THE INVENTION

Aging skin is the result of more than just chronological age. Skin is exposed to various environmental stresses, such as UV rays, which cause free radicals to form in the skin. The degree of UV protection afforded by a composition is directly related to the amount and type of sunscreen actives present therein. The more sunscreen actives present, the greater the degree of UV protection. It is highly desirous for a sunscreen to offer a high degree of both UVA and UVB protection while being mild on the skin and cosmetically elegant. Mineral sunscreen actives, such as titanium dioxide and zinc oxide, are known to be efficient filters and especially mild on the skin. Consequently cosmetic companies seek to produce sunscreen formulations that utilize mineral sunscreen actives in place of organic filters. However, formulating sunscreens with inorganic filters/sunscreen actives presents a unique challenge because the inorganic filters have a tendency to re-agglomerate into large clusters. Due to this re-agglomeration tendency, although formulae with a high concentration of mineral actives achieve desired high PFA/SPF values, the formulae are often draggy and whitening, forming a thick residual layer on the skin.

Recently, there has been an explosion of metastable products on the market that promise lighter textures. However, these formulae rely on high loads of cyclosiloxanes to obtain fluidity and often greasy pigment dispersions to ensure efficacy. To thicken their formulae/stabilize their dispersions, they have relied upon traditional thickeners used in skin and sun care such as DryFlo, corn Starch, carbomers and Xanthum Gum.

It is an object of the present invention to provide a mineral sunscreen composition with high PFA/SPF properties that is stable and avoids re-agglomeration of sunscreen actives thereby providing a non-whitening and cosmetically elegant composition.

BRIEF SUMMARY OF THE INVENTION

The present invention is directed to a mineral sunscreen composition containing:
(a) at least one oil phase thickening agent chosen from an activated clay;
(b) at least one substantially solid form dispersing aid;
(c) at least one non-volatile solvent;
(d) at least one inorganic sunscreen active;
(e) at least one emulsifier;
(f) at least one volatile solvent; and
(g) water, wherein the activated clay and the substantially solid form dispersing aid are present in the composition at a ratio by weight ranging from greater than 1:4 to less than 1:10.

In another embodiment, the present invention is directed to a mineral sunscreen composition containing:
(a) from about 0.1% to about 1.25% by weight of at least one oil phase thickening agent chosen from an activated clay selected from the group consisting of disteardimonium hectorite, stearalkonium hectorite, quaternium-18 bentonite, quaternium-18 hectorite, and benzalkonium bentonite;
(b) from about 1% to about 5% by weight of at least one substantially solid form dispersing aid comprising talc;
(c) from about 30% to about 50% by weight of at least one non-volatile solvent;
(d) from about 5% to about 15% by weight of at least one inorganic sunscreen active;
(e) from about 1% to about 8% by weight of at least one emulsifier;
(f) from about 3% to about 10% by weight of at least one volatile solvent; and
(g) remainder by weight water, wherein the weights of (a)-(g) are based on the total weight of the composition; and wherein (a) and (b) are present in the composition in a ratio by weight ranging from greater than 1:4 to less than 1:10.

The present invention is also directed to a method for protecting a keratinous substrate from UV rays by topically applying the above-disclosed composition onto the substrate.

DETAILED DESCRIPTION OF THE INVENTION

The present invention is based on the surprising and unexpected finding that the combination of activated clay, with a solid form dispersing aid synergistically inhibits the agglomeration of inorganic sunscreen actives present in a sunscreen composition. This inhibition of agglomeration results in improved photo protection efficacy, thereby protecting skin from UV rays while remaining cosmetically elegant and non-whiting in application. The present invention's composition surprising and unexpectedly results in a unique synergy between the activated clay and the solid form dispersing aid that provides stability to the composition and prevents agglomeration of the inorganic sunscreen actives. It has been particularly found that the activated clay to solid form dispersing agent utilized in a ratio by weight ranging from greater than about 1:4 up to less than about 1:10, including at ratios of 1:5, 1:6, 1:7, 1:8, 1:9 and less than 1:10. Owing to this synergistic effect between the activated clay and the solid form dispersing aid at the forgoing ratio in particularly, a high load of inorganic sunscreen actives, zinc oxide and/or titanium dioxide, can be employed resulting in a composition with very strong UVB and UVA protection that is surprisingly non-whitening with a high degree of silkiness and spreadability.

The proposed composition employs inorganic sunscreen actives/filters in composition with activated organoclay and the solid form dispersing aid. Unlike traditional thickeners, it has been found that activated clay structure entraps the sunscreen microparticles and prevents them from reagglomerating and settling while the product is not being used. Once the product is applied, the yield point of the structures is surpassed and they open, evenly spreading the sunscreen filter particles on the skin. It has been surprisingly and unexpectedly found that the micro-sized talc prevents the mineral sunscreen filters from reagglomerating due to its platelet structure. Through the synergistic combination of the activated organoclay and the micro-sized talc, the sunscreen filters remain well-dispersed in the formulation, thus decreasing the formation of large agglomerates that would cause whitening on the skin when the product is applied.

Other than in the operating examples, or where otherwise indicated, all numbers expressing quantities of ingredients and/or reaction conditions or ratios are to be understood as being modified in all instances by the term "about".

A "physiologically acceptable medium" means a medium which is not toxic and can be applied to the skin, lips, hair, scalp, lashes, brows, nails or any other cutaneous region of the body. The composition of the invention may especially constitute a cosmetic or dermatological composition.

The phrase "metastable" refers generally to a fluid, metastable formulation that can, after time, have a slight separation on the surface but can be remixed/re-emulsified with shaking.

Activated Clay

The composition contains at least one oil phase thickening agent chosen from activated clay. The clay is preferably an organoclay dispersed in oil with an organic solvent, and an organic activator (polar swelling agent).

Organoclays generally include those which are the reaction products of bentonite clays and quaternium ammonium salts, hectorite clays and quaternium ammonium salts, or montmorillonite clays and quaternium ammonium salts. The organoclay may be selected from the group consisting of disteardimonium hectorite, stearalkonium hectorite, quaternium-18 bentonite, quaternium-18 hectorite, and benzalkonium bentonite.

Suitable organic activators include, but are not limited to, lower monohydric alcohols such as ethanol and isopropyl alcohol; polar esters such as propylene carbonate; water; and the like.

Suitable organic solvents include, but are not limited to, natural oils, such as castor oil and lanolin oil; hydrocarbons, such as mineral oil, petroleum distillates, and isododecane; esters, such as isopropyl palmitate, isopropyl myristate and C12-C15 alkyl benzoate; diesters, such as propylene glycol dicaprylate; volatile silicones such as cyclomethicone; polymeric silicones such as dimethicone; and the like.

The organoclay component may be prepared by combining an organoclay, a nonpolar carrier and a polar swelling agent in a homogenizer-type mixer. Alternatively, commercial preparations comprising organoclays, nonpolar carriers, and polar swelling agents may be used. Preferably, a bentonite clay, hectorite clay, and montmorillonite clay is chosen for use in the composition. Most preferably the clay is a disteardimonium hectorite and propylene carbonate, or a gel formed by way of a dispersion of fully activated disteardimonium hectorite, a non-animal origin hectorite organoclay, in isododecane and propylene carbonate, such as those commercially available under the trade name Bentone Gel® (Elementis Specialties, Inc., Hightstown, N.J.).

The activated clay is generally present in the composition of the present invention in an amount ranging from about 0.01% to about 7.5% by weight; such as from about 0.05% to about 2.5% by weight; such as from about 0.1% to about 1.25% by weight, based on the total weight of the composition.

Substantially Solid Form Dispersing Aid

The composition also contains at least one substantially solid form dispersing aid. The dispersing aid may be mineral or organic, and lamellar, platelet-shaped or flake.

Dispersing agents generally include talc, mica, barium sulfate, kaolin, lauroyllysine, starch, boron nitride, precipitated calcium carbonate, magnesium carbonate, magnesium hydrogen carbonate, hydroxyapatite, montmorillonite (for example Gel White H from Rookwood Additives), polytetrafluoroethylene (PTFE) wax particles (for instance Ceridust 9205 F from Clariant, or Fluoropure 103 C from Shamrock Technologies), calcium sulfate (for instance Prestia PR306 from Lafarge Prestia), pumice powder (for instance O-D decontaminated pumice from Eyraud), bismuth oxychloride, bismuth oxychloride, perlite (for instance Optima 1430 OR from World Minerals), glass particles especially about 10 microns in size and about 0.4 micron thick, for instance those sold under the references MTD010FYX(6001) or MTD010FYX(6009) by Nippon Sheet Glass, about 25 microns in size and about 0.4 micron thick, for instance those sold under the references MTD025FYX(6002) or MTD025FYX(6010) by Nippon Sheet Glass, silica and titanium dioxide sol/gel particles (for instance NLT30H2WA from Nippon Sheet Glass), mica and titanium dioxide particles, for instance Blancsealer from Merck.

The dispersing aid is preferably chosen from lauroyl lysine, mica, sericite, talc, polytetrafluoroethylene (PTFE), boron nitride, kaolin, oxychloride bismuth, aluminum oxide, silicon, perlite, oxychloride bismuth, barium sulfate, glass particles, zincoxide, mica-barium sulfate, and synthetic mica, silica.

Most preferably the dispersing aid is micro-talc (for instance Micro Ace P3 by Nippon Talc). Micro-talc particle sizes preferably range from 1 to 300 μm; most preferably ranging from 2 to 15 μm. The talc particles may be used alone or in combination. Hybrid powders may be employed, including talc in combination with titanium dioxide, aluminum oxide, and silicon (for instance Coverleaf AR80 from Presperse LLC), talc in combination with aluminum oxide and silicone dioxide (for instance Coverleaf AR100). Other hybrid powder contemplated include zinc oxide on mica-barium sulfate (for instance Shadeleaf A from Merck), titanium dioxide on mica (for instance Blancsealer from Merck), titanium dioxide on silica (for instance NL T30H2WA from Nippon Sheet Glass), and titanium dioxide on mica-barium sulfate (for instance Naturaleaf powder from Merck).

It should be noted that the substantially solid form dispersing aid is preferably platelet-like in form so as to facilitate the inhibition of agglomeration between the inorganic sunscreen actives present in the composition.

The substantially solid form dispersing aid is generally present in the composition of the present invention in an amount ranging from about 0.1% to about 30% by weight; such as from about 0.5% to about 10% by weight; such as from about 1% to about 5% by weight, based on the total weight of the composition.

Further, it has been particularly found that the activated clay to solid form dispersing agent (particularly talc) is to be utilized in a ratio by weight ranging from greater than about 1:4 up to less than about 1:10, including at ratios of 1:5, 1:6, 1:7, 1:8, 1:9 and less than 1:10. Preferably, the ratio is greater than or equal to 1:5 up to less than or equal to about 1:9.

Non-Volatile Solvent

The composition also contains at least one non-volatile solvent. The non-volatile solvent is preferably chosen from silicone oils, both functionalised and non-functionalised, hydrocarbon oils and mixtures thereof.

It is also pointed out that, for the purposes of the invention, the term "non-volatile" generally means a solvent that remains on the keratin substrate at room temperature and atmospheric pressure at least for several hours.

Examples of suitable non-volatile solvents include, but are not limited to, polar oils and non-polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, and also including, for example, octyldodecyl neopentanoate, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

Examples of non-volatile solvents also include non-volatile silicones such as dimethicone fluids having viscosity values of equal to or greater than 300 cst.

Suitable non-volatile silicone oils that may be used include, but are not limited to, linear polydimethylsiloxanes (PDMSs), that are liquid at room temperature; polydimethylsiloxanes comprising alkyl, alkoxy or phenyl groups, which are pendent and/or at the end of a silicone chain, these groups each containing from 2 to 24 carbon atoms; phenylsilicones, for instance phenyl trimethicones, phenyl dimethicones, phenyl trimethylsiloxydiphenylsiloxanes, diphenyl dimethicones, diphenyl methyldiphenyl trisiloxanes, 2-phenylethyl trimethylsiloxysilicates, trimethyl pentaphenyl trisiloxane, tetramethyl hexaphenyl trisiloxane.

The non-volatile solvent is generally present in the composition of the present invention in an amount ranging from about 5% to about 80% by weight; such as from about 10% to about 50% by weight; such as from about 15% to about 30% by weight, based on the total weight of the composition.

Inorganic Sunscreen Active

The composition also contains at least one inorganic sunscreen active chosen from UVA-active and/or UVB-active mineral/inorganic photoprotective agents.

The sunscreen actives of the composition of the present invention are mineral photoprotective agents, or mixtures thereof. Suitable physical blockers include, but are not limited to, cerium oxides; chromium oxides; cobalt oxides; iron oxides; red petrolatum; silicone-treated titanium dioxide; titanium dioxide; zinc oxide; zirconium oxide; and mixtures thereof.

Physical sunscreens, such as titanium dioxide or zinc oxide are preferred. Preferably, ultrafine titanium dioxide of the rutile type is used. In a most preferred embodiment, the titanium dioxide has a primary particle size of about 0.08 to about 0.3 microns [about 80 nm to about 300 nm], as measured by laser diffraction, on a volume basis. The surface area of the primary particles of ultrafine titanium dioxide is preferably in the range of from about 35 to about 45 $m^2/g$. The UFTR grade (ultrafine) of titanium oxide, such as is commercially available from, for example, U.S. Cosmetics Corp., Dayville, Conn., is suitably used in the present invention.

Most preferably, ultrafine titanium dioxide coated with an agent, such as, for example, aluminum oxide, to provide light stability is used in the makeup composition. The coated particles may also be surface treated to reduce surface activity and, hence agglomeration. Surface treatment of titanium dioxide or titanium dioxide coated with alumina includes, for example, a silicone surface treatment, preferably a dimethicone treatment using dimethicone oil. Aluminum oxide coated, dimethicone oil treated ultrafine titanium dioxide is commercially available, such as SAT-ID-UFTR titanium dioxide, from U.S. Cosmetics Corp., Dayville, Conn.

Examples of mineral photoprotective agents are chosen from pigments (1 nm to 750000 nm) and even more preferably nanopigments (mean size of the primary particles: generally between 5 nm and 100 nm and preferably between 10 nm and 50 nm) and/or combinations thereof, of treated or untreated metal oxides such as, for example, nanopigments of titanium oxide (amorphous or crystallized in rutile and/or anatase form), of iron oxide, of zinc oxide, of zirconium oxide or of cerium oxide.

The treated nanopigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal (titanium or aluminium) alkoxides, poly-ethylene, silicones, proteins (collagen or elastin), alkanolamines, silicon oxides, metal oxides, sodium hexametaphosphate, alumina or glycerol.

The treated nanopigments may more particularly be titanium oxides treated with:

silica and alumina, such as the products "Microtitanium Dioxide MT 500 SA" and "Microtitanium Dioxide MT 100 SA" from the company Tayca, and the products "Tioveil Fin", "Tioveil OP", "Tioveil MOTG" and "Tioveil IPM" from the company Tioxide, alumina and aluminium stearate, such as the product "Microtitanium Dioxide MT 100 T" from the company Tayca, and the products "Solaveil CT" from the company Croda, alumina and aluminium laurate, such as the product "Microtitanium Dioxide MT 100 S" from the company Tayca, iron oxides and iron stearate, such as the product "Microtitanium Dioxide MT 100 F" from the company Tayca, silica, alumina and silicone, such as the products "Microtitanium Dioxide MT 100 SAS", "Microtitanium Dioxide MT 600 SAS" and "Microtitanium Dioxide MT 500 SAS" from the company Tayca, sodium hexametaphosphate, such as the product "Microtitanium Dioxide MT 150 W" from the company Tayca, octyltrimethoxysilane, such as the product "T-805" from the company Degussa, alumina and stearic acid, such as the product "UVT-M160" from the company Kemira, alumina and glycerol, such as the product "UVT-M212" from the company Kemira, alumina and silicone, such as the product "UVT-M262" from the company Kemira.

Other titanium oxide nanopigments treated with a silicone are preferably $TiO_2$ treated with octyltrimethylsilane and for which the mean size of the elementary particles is between 25 and 40 nm, such as the product sold under the trade name "T805" by the company Degussa Silices, $TiO_2$ treated with a polydimethylsiloxane and for which the mean size of the elementary particles is 21 nm, such as the product sold under the trade name "70250 Cardre UF TiO2SI3" by the company Cardre, anatase/rutile $TiO_2$ treated with a polydimethylhydrogenosiloxane and for which the mean size of the elementary particles is 25 nm, such as the product sold under the trade name "Microtitanium Dioxide USA Grade Hydrophobic" by the company Color Techniques.

The uncoated titanium oxide nanopigments are sold, for example, by the company Tayca under the trade names "Microtitanium Dioxide MT 500 B" or "Microtitanium Dioxide MT 600 B", by the company Degussa under the name "P 25", by the company Wackher under the name "Oxyde de titane transparent PW", by the company Myoshi Kasei under the name "QFTR", by the company Tomen under the name "ITS" and by the company Tioxide under the name "Tioveil AQ".

The uncoated zinc oxide nanopigments are, for example:
microfine zinc oxide such as those sold under the name "Z-Cote" by the company Sunsmart or BASF—those sold under the name "Nanox" by the company Elementis;
those sold under the name "Nanogard WCD 2025" by the company Nanophase Technologies.

The coated zinc oxide nanopigments are, for example:
treated zinc oxides, such as those sold under the name "Z-COTE HP" by the company Sunsmart or BASF;
those sold under the name "Zinc Oxide CS-5" by the company Toshibi (ZnO coated with polymethylhydrogenosiloxane);
those sold under the name "Nanogard Zinc Oxide FN" by the company Nanophase Technologies (as a 40% dispersion in Finsolv TN, $C_{12}$-$C_{15}$ alkyl benzoate);
those sold under the name "Daitopersion ZN-30" and "Daitopersion ZN-50" by the company Daito (dispersions in cyclopolymethylsiloxane/oxyethylenated polydimethylsiloxane, containing 30% or 50% of nanozinc oxides coated with silica and polymethylhydrogenosiloxane);
those sold under the name "NFD Ultrafine ZNO" by the company Daikin (ZnO coated with perfluoroalkyl phosphate and copolymer based on perfluoroalkylethyl as a dispersion in cyclopentasiloxane);
those sold under the name "SPD-Z1" by the company Shin-Etsu (ZnO coated with silicone-grafted acrylic polymer, dispersed in cyclodimethylsiloxane);
those sold under the name "Escalol Z100" by the company ISP (alumina-treated ZnO dispersed in an ethylhexyl methoxycinnamate/PVP-hexadecene/methicone copolymer mixture);
those sold under the name "Fuji ZNO-SMS-10" by the company Fuji Pigment (ZnO coated with silica and polymethylsilsesquioxane);
those sold under the name "Nanox Gel TN" by the company Elementis (ZnO dispersed at a concentration of 55% in $C_{12}$-$C_{15}$ alkyl benzoate with hydroxystearic acid polycondensate).

The uncoated cerium oxide nanopigments are sold under the name "Colloidal Cerium Oxide" by the company Rhone-Poulenc.

The uncoated iron oxide nanopigments are sold, for example, by the company Arnaud under the names "Nanogard WCD 2002 (FE 45B)", "Nanogard Iron FE 45 BL AQ", "Nanogard FE 45R AQ" and "Nanogard WCD 2006 (FE 45R)" or by the company Mitsubishi under the name "TY-220", The coated iron oxide nanopigments are sold, for example, by the company Arnaud under the names "Nanogard WCD 2008 (FE 45B FN)", "Nanogard WCD 2009 (FE 45B 556)", "Nanogard FE 45 BL 345" and "Nanogard FE 45 EL" or by the company BASF under the name "Transparent Iron Oxide".

Mention may also be made of mixtures of metal oxides, especially of titanium dioxide and of cerium dioxide, including the silica-coated equal-weight mixture of titanium dioxide and of cerium dioxide, sold by the company Ikeda under the name "Sunveil A", and also the alumina, silica and silicone-coated mixture of titanium dioxide and of zinc dioxide, such as the product "M 261" sold by the company Kemira, or the alumina, silica and glycerol-coated mixture of titanium dioxide and of zinc dioxide, such as the product "M 211" sold by the company Kemira.

The nanopigments may be introduced into the compositions according to the invention in unmodified form or in the form of pigmentary paste, i.e. as a mixture with a dispersant, as described, for example, in document GB-A-2 206 339.

The inorganic sunscreen active is generally present in the composition of the present invention in an amount ranging from about 0.1% to about 50% by weight; such as from about 1% to about 20% by weight; such as from about 5% to about 15% by weight, based on the total weight of the composition.

In order to achieve maximum sunscreen efficacy, preferably substantially solid form dispersing aid and inorganic sunscreen active are employed in a ratio by weight ranging from about 1:1 to 1:30, preferably from about 1:3 to 1:25, and most preferably from about 1:5 to 1:20

Emulsifier

The composition also contains at least one emulsifier. Suitable emulsifiers that can be used according to the present invention include, but are not limited to, nonionic, cationic, anionic, and zwitterionic emulsifiers. Alternatively, suitable emulsifiers according to the present invention include, but are not limited to, acyl lactylates, alkyl phosphates, carboxylic acid copolymers, esters and ethers of glucose, esters of glycerin, esters of, esters of sorbitan anhydrides, esters of sorbitol, ethoxylated ethers, ethoxylated alcohols, fatty acid amides, fatty acid esters of polyethylene glycol, fatty esters of polypropylene glycol, polyoxyethylene fatty ether phosphates, soaps, alkoxylated polydimethylsiloxanes, and mixtures thereof.

Preferably, the emulsifier is chosen from emulsifying crosslinked siloxane elastomers such as Dimethicone/PEG-10/15 Crosspolymer commercially available from the Shin-Etsu Company as KSG-210, Dimethicone/Polyglycerin-3 Crosspolymer commercially available from the Shin-Etsu Company as KSG 710, Lauryl PEG-15 Dimethicone/Vinyl Dimethicone Crosspolymer commercially available from the Shin-Etsu Company as KSG-31, PEG-12 Dimethicone Crosspolymer, commercially available from the Dow-Corning Company as DC 9011. In one embodiment, the compound useful as an emulsifier is Dimethicone/PEG-10/15 Crosspolymer. For examples of other suitable emulsifiers that can be used according to the present invention, see, for example, McCutcheon's, Detergents and Emulsifiers, North American Edition (2003), Allured Publishing Corporation, the entire contents of which are hereby incorporated by reference.

The compositions according to the invention may be prepared according to techniques that are well known to those skilled in the art, in particular those intended for the preparation of emulsions of oil-in-water, water-in-oil, silicone-in-water and/or water-in-silicone type. They may be in particular in the form of a simple or complex emulsion (O/W, W/O, O/W/O, W/O/W and/or W/Si emulsions) such as a cream or a milk, in the form of a gel or a cream-gel, or in the form of a lotion, a powder or a solid tube, and may optionally be packaged as an aerosol and may be in the form of a mousse or a spray. These compositions are prepared according to the usual methods.

The compositions according to the invention are preferably in the form of an oil-in-water or water-in-oil emulsion.

As emulsifying surfactants that may be used for the preparation of the W/O emulsions, examples that may be mentioned include sorbitan, glycerol or sugar alkyl esters or ethers; silicone surfactants, for instance dimethicone copolyols, such as the mixture of cyclomethicone and of dimethicone copolyol, sold under the name "DC 5225 C" by the company Dow Corning, and alkyldimethicone copolyols such as laurylmethicone copolyol sold under the name "Dow Corning 5200 Formulation Aid" by the company Dow Corning; cetyldimethicone copolyol, such as the product sold under the name Abil EM 90R by the company Goldschmidt, and the mixture of cetyldimethicone copolyol, of polyglyceryl isostearate (4 mol) and of hexyl laurate, sold under the name Abil WE 09 by the company Goldschmidt. One or more co-emulsifiers may also be added thereto, which may be chosen advantageously from the group comprising polyol alkyl esters. Polyol alkyl esters that may especially be mentioned include glycerol and/or sorbitan esters, for example polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

For the O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alkyl ethers; sugar esters, for instance sucrose stearate; fatty alkyl ethers of sugars, especially polyalkylglucosides (APG) such as decylglucoside and laurylglucoside sold, for example, by the company Henkel under the respective names Plantaren 2000 and Plantaren 1200, cetostearyl glucoside optionally as a mixture with cetostearyl alcohol, sold, for example, under the name Montanov 68 by the company SEPPIC, under the name Tegocare CG90 by the company Goldschmidt and under the name Emulgade KE3302 by the company Henkel, and also arachidyl glucoside, for example in the form of a mixture of arachidyl alcohol, behenyl alcohol and arachidyl glucoside, sold under the name Montanov 202 by the company SEPPIC. According to one particular embodiment of the invention, the mixture of the alkylpolyglucoside as defined above with the corresponding fatty alcohol may be in the form of a self-emulsifying composition as described, for example, in document WO-A-92/06778.

In a particularly preferred embodiment of the invention, the subject compositions are formulated as water-in-silicone or silicone-in-water emulsions in which the continuous oily phase comprises at least one silicone oil. When the compositions of the invention are formulated as water-in-silicone emulsions, the silicone oils are preferably present in a proportion of at least 5 percent and preferably ranging from 10 percent to 45 percent by weight with respect to the total weight of the emulsion. The fatty phase of the water-in-oil emulsions according to the invention can additionally comprise one or more hydrocarbon-comprising oil(s) in a proportion preferably ranging up to 40 percent by weight with respect to the total weight of the fatty phase of the emulsion.

Oils that may be used in the W/Si or Si/W composition may include for example: silicone oils, for instance volatile or non-volatile polymethylsiloxanes (PDMS) with a linear or cyclic silicone chain, which are liquid or pasty at room temperature, especially cyclopolydimethylsiloxanes (cyclomethicones) such as cyclohexasiloxane; polydimethyl-siloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyl-trimethylsiloxydiphenyl-siloxanes, diphenyl dimethicones, diphenylmethyl-diphenyltrisiloxanes or 2-phenylethyl trimethylsiloxy silicates, and polymethylphenylsiloxanes; mixtures thereof. Particularly representative of such oils are volatile silicone oils, such as cyclomethicones, in order to impart greater fastness towards water of the coloration on the skin, easier and more homogeneous spreading of the composition and shorter drying times.

For the W/Si emulsions, examples of emulsifiers generally include polyether-modified silicones having a long chain of dimethyl siloxane units which carry polyethoxy-polypropoxy units in the chain and at the ends. Examples include cyclopentasiloxane PEG/PPG-18/18 dimethicone, PEG-12 Dimethicone, and PEG/PPG-19/19 Dimethicone sold by Dow Corning under the name Dow Corning® BY 11-030.

The emulsifier is generally present in the composition of the present invention in an amount ranging from about 0% to about 15% by weight; such as from about 0.5% to about 10% by weight; such as from about 1% to about 8% by weight, based on the total weight of the composition.

Volatile Solvent

The composition also contains at least one volatile solvent.

The expression "volatile solvent" means any non-aqueous medium capable of evaporating on contact with the skin or the lips in less than one hour at room temperature and atmospheric pressure.

Examples of suitable volatile solvents include, but are not limited to, volatile hydrocarbon-based oils such as, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate, alcohols, and their mixtures. Preferably, the volatile hydrocarbon-based oils have a flash point of at least 40° C.

Examples of volatile hydrocarbon-based oils include, but are not limited to those given in Table 1 below.

TABLE 1

| Compound | Flash Point (° C.) |
|---|---|
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatile solvent may also be chosen from volatile silicone oils, which may be linear or cyclic, having a viscosity, at room temperature, of less than or equal to 6 cSt, and having from 2 to 7 silicon atoms, optionally substituted with alkyl or alkoxy groups of 1 to 10 carbon atoms.

Examples of suitable volatile silicone oils include, but are not limited to, those listed in Table 2 below.

TABLE 2

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

Further examples of volatile silicone oils which may be incorporated into cosmetic compositions according to the invention include cyclic volatile silicones. Preferably, the cyclic volatile silicone is cyclopentasiloxane or cyclohexasiloxane. Examples of commercially available volatile silicone oils include the following cyclomethicones: Dow Corning 200, Dow Corning 244, Dow Corning 245, Dow Corning 344, and Dow Corning 345 (commercially available from Dow Corning Corp.); SF-1204 and SF-1202 Silicone Fluids (commercially available from G. E. Silicones), GE 7207 and 7158 (commercially available from General Electric Co.); and SWS-03314 (commercially available from SWS Silicones Corp.). Other examples of commercially available methyl silsesquioxanes available as TMF 1.5 fluid from Shin-Etsu Chemical Co; SILCARE SILICONES, for example phenyl substituted silsesquioxanes available as Silcare 15M60, n-Octyl substituted silsesquioxanes available as Silcare 31M60 and 31M50, hexyl methicone, caprylyl methicone and lauryl methicone available as Silcare 41M10, 41M15 and 41M20, respectively from Clariant.

Other suitable solvents include, but are not limited to, organic solvents which are liquid at ambient temperature. Examples of suitable volatile solvents include, but are not limited to, ketones such as methyl ethyl ketone, methyl isobutyl ketone, diisobutyl ketone, isophorone, cyclohexanone or acetone; alcohols, such as ethanol, isopropanol, diacetone alcohol, 2-butoxyethanol or cyclohexanol; glycols, such as ethylene glycol, propylene glycol, pentylene glycol or glycerol; propylene glycol ethers, such as propylene glycol monomethyl ether, propylene glycol monomethyl ether acetate or dipropylene glycol mono(n-butyl)ether; short-chain esters (having a total of 2 to 7 carbon atoms), such as ethyl acetate, methyl acetate, propyl acetate, n-butyl acetate or isopentyl acetate; alkanes, such as decane, heptane, dodecane or cyclohexane; aldehydes, such as benzaldehyde or acetaldehyde; and their mixtures. Most preferred are short-chain esters (having a total of from 2 to 8 carbon atoms).

The volatile solvent may also be chosen from linear or branched hydrocarbons of mineral or synthetic origin, and derivatives thereof, such as liquid petroleum jelly and hydrogenated polyisobutene such as Parléam® oil; $C_8$-$C_{16}$ branched alkanes or isoalkanes (also known as isoparaffins), isododecane, isodecane and isohexadecane, such as for example the isoparaffins sold under the trade names Isopar by Exxon Chemical or the oils sold under the trade names Permethyl by Presperse; and mixtures thereof; volatile linear alkanes comprising from 7 to 17 carbon atoms such as undecane and tridecane.

A volatile linear alkane suitable for the invention is liquid at ambient temperature (around 25° C.) and at atmospheric pressure (760 mmHg).

The expression "volatile linear alkane", suitable for the invention, is understood to mean a cosmetic linear alkane capable of evaporating on contact with the skin in less than one hour, at ambient temperature (25° C.) and atmospheric pressure (760 mmHg, that is to say 101 325 Pa), that is liquid at ambient temperature, and that has, in particular, an evaporation rate ranging from 0.01 to 15 mg/cm$^2$/min at ambient temperature (25° C.) and atmospheric pressure (760 mmHg).

Preferably, the "volatile linear alkanes" suitable for the invention have an evaporation rate ranging from 0.01 to 3.5 mg/cm$^2$/min at ambient temperature (25° C.) and atmospheric pressure (760 mmHg).

Preferably, the "volatile linear alkanes" suitable for the invention have an evaporation rate ranging from 0.01 to 1.5 mg/cm$^2$/min at ambient temperature (25° C.) and atmospheric pressure (760 mmHg).

More preferably, the "volatile linear alkanes" suitable for the invention have an evaporation rate ranging from 0.01 to 0.8 mg/cm$^2$/min at ambient temperature (25° C.) and atmospheric pressure (760 mmHg).

More preferably, the "volatile linear alkanes" suitable for the invention have an evaporation rate ranging from 0.01 to 0.3 mg/cm$^2$/min at ambient temperature (25° C.) and atmospheric pressure (760 mmHg).

More preferably, the "volatile linear alkanes" suitable for the invention have an evaporation rate ranging from 0.01 to 0.12 mg/cm$^2$/min at ambient temperature (25° C.) and atmospheric pressure (760 mmHg).

The evaporation rate of a volatile alkane according to the invention (and more generally of a volatile solvent) may especially be evaluated by means of the protocol described in WO 06/013413, and more particularly by means of the protocol described below.

Introduced into a crystallizing dish (diameter: 7 cm), placed on a balance that is located in a chamber of around 0.3 m$^3$, the temperature (25° C.) and hygrometry (50% relative humidity) of which are regulated, are 15 g of volatile hydrocarbon-based solvent.

The liquid is left to evaporate freely, without being stirred, ventilation being provided by a fan (PAPST-MOTOREN, reference 8550 N, rotating at 2700 rpm) placed in a vertical position above the crystallizing dish containing the volatile hydrocarbon-based solvent, the blades being directed towards the crystallizing dish, at a distance of 20 cm relative to the base of the crystallizing dish.

The mass of volatile hydrocarbon-based solvent remaining in the crystallizing dish is measured at regular time intervals.

The evaporation profile of the solvent is then obtained by plotting the curve of the amounts of product evaporated (in mg/cm$^2$) as a function of the time (in min).

Then the evaporation rate, which corresponds to the tangent at the origin of the curve obtained, is calculated. The evaporation rates are expressed as mg of volatile solvent evaporated per unit area (cm$^2$) and per unit time (minutes).

According to one preferred embodiment, the "volatile linear alkanes" suitable for the invention have a non-zero vapour pressure (also known as saturation vapour pressure) at ambient temperature, in particular a vapour pressure ranging from 0.3 Pa to 6000 Pa.

Preferably, the "volatile linear alkanes" suitable for the invention have a vapour pressure ranging from 0.3 to 2000 Pa at ambient temperature (25° C.).

Preferably, the "volatile linear alkanes" suitable for the invention have a vapour pressure ranging from 0.3 to 1000 Pa at ambient temperature (25° C.)

More preferably, the "volatile linear alkanes" suitable for the invention have a vapour pressure ranging from 0.4 to 600 Pa at ambient temperature (25° C.).

Preferably, the "volatile linear alkanes" suitable for the invention have a vapour pressure ranging from 1 to 200 Pa at ambient temperature (25° C.)

More preferably, the "volatile linear alkanes" suitable for the invention have a vapour pressure ranging from 3 to 60 Pa at ambient temperature (25° C.)

According to one embodiment, a linear volatile alkane suitable for the invention may have a flashpoint in the range that varies from 30 to 120° C., and more particularly from 40 to 100° C. The flashpoint is, in particular, measured according to the ISO 3679 standard.

The volatile linear alkanes comprise from 7 to 17 carbon atoms, in particular from 7 to 15 carbon atoms, better still from 9 to 15 carbon atoms, and more particularly from 11 to 13 carbon atoms.

The volatile linear alkanes in accordance with the invention may advantageously be of plant origin.

According to one embodiment, an alkane suitable for the invention may be a volatile linear alkane comprising from 7 to 14 carbon atoms.

Preferably, the "volatile linear alkanes" suitable for the invention comprise from 8 to 14 carbon atoms.

Preferably, the "volatile linear alkanes" suitable for the invention comprise from 9 to 14 carbon atoms.

Preferably, the "volatile linear alkanes" suitable for the invention comprise from 10 to 14 carbon atoms.

Preferably, the "volatile linear alkanes" suitable for the invention comprise from 11 to 14 carbon atoms.

According to one advantageous embodiment, the "volatile linear alkanes" suitable for the invention have an evaporation rate, as defined above, ranging from 0.01 to 3.5 mg/cm$^2$/min at ambient temperature (25° C.) and atmospheric pressure (760 mmHg) and comprise from 8 to 14 carbon atoms.

A volatile linear alkane suitable for the invention may advantageously be of plant origin.

Preferably, the volatile linear alkane or the mixture of volatile linear alkanes present in the composition according to the invention comprises at least one $^{14}$C isotope of carbon (carbon-14), in particular the $^{14}$C isotope may be present in a $^{14}$C/$^{12}$C ratio greater than or equal to $1\times10^{-16}$, preferably greater than or equal to $1\times10^{-15}$, more preferably greater than or equal to $7.5\times10^{-14}$, and better still greater than or equal to $1.5\times10^{-13}$. Preferably, the $^{14}$C/$^{12}$C ratio ranges from $6\times10^{-13}$ to $1.2\times10^{-12}$.

The amount of $^{14}$C isotopes in the volatile linear alkane or the mixture of volatile linear alkanes may be determined by methods known to a person skilled in the art such as the Libby counting method, liquid scintillation spectrometry or else accelerator mass spectrometry.

Such alkanes may be obtained, directly or in several steps, from a plant raw material such as an oil, a butter, a wax, etc.

As examples of volatile linear alkanes suitable for the invention, mention may be made of those described in patent application WO 2007/068371 or WO 2008/155059 by Cognis (mixtures of different alkanes that differ by at least one carbon).

These alkanes are obtained from fatty alcohols that are themselves obtained from coconut oil or palm oil.

By way of example of a volatile linear alkane suitable for the invention, mention may be made of n-heptane (C7), n-octane (C8), n-nonane (C$_9$), n-decane (C$_{10}$), n-undecane (C$_{11}$), n-dodecane (C$_{12}$), n-tridecane (C$_{13}$), n-tetradecane (C$_{14}$), n-pentadecane (C$_{15}$), n-hexadecane (C$_{16}$) and n-heptadecane (C$_{17}$) and mixtures thereof.

According to one particular embodiment, the volatile linear alkane is chosen from n-nonane, n-undecane, n-dodecane, n-tridecane, n-tetradecane, and mixtures thereof.

According to one preferred mode, mention may be made of the mixtures of n-undecane (C$_{11}$) and of n-tridecane (C$_{13}$) obtained in examples 1 and 2 of application WO 2008/155059 by Cognis.

Mention may also be made of n-dodecane (C$_{12}$) and n-tetradecane (C$_{14}$) sold by Sasol respectively under the references PARAFOL 12-97 and PARAFOL 14-97, and also mixtures thereof.

The volatile linear alkane could be used alone.

Alternatively or preferably a mixture of at least two different volatile linear alkanes could be used, that differ from one another by a carbon number n of at least 1, in particular that differ from one another by a carbon number of 1 or 2.

According to a first embodiment, use is made of a mixture of at least two different volatile linear alkanes comprising from 10 to 14 carbon atoms that differ from one another by a carbon number of at least 1. By way of examples, mention may especially be made of the C$_{10}$/C$_{11}$, C$_{11}$/C$_{12}$ or C$_{12}$/C$_{13}$ mixtures of volatile linear alkanes.

According to another embodiment, use is made of a mixture of at least two different volatile linear alkanes comprising from 10 to 14 carbon atoms that differ from one another by a carbon number of at least 2. By way of examples, mention may especially be made of the C$_{10}$/C$_{12}$ or C$_{12}$/C$_{14}$ mixtures of volatile linear alkanes, for an even carbon number n and the C$_{11}$/C$_{13}$ mixture for an odd carbon number n.

According to one preferred mode, use is made of a mixture of at least two different volatile linear alkanes comprising from 10 to 14 carbon atoms that differ from one another by a carbon number of at least 2, and in particular a C$_{11}$/C$_{13}$ mixture of volatile linear alkanes or a C$_{12}$/C$_{14}$ mixture of the volatile linear alkanes.

Other mixtures combining more than 2 volatile linear alkanes according to the invention, such as for example a mixture of at least 3 different volatile linear alkanes comprising from 7 to 14 carbon atoms that differ from one another by a carbon number of at least 1, are also part of the invention, but the mixtures with 2 volatile linear alkanes according to the invention are preferred (binary mixtures), said 2 volatile linear alkanes preferably representing more than 95% and better still more than 99% by weight of the total content of volatile linear alkanes in the mixture. According to one particular mode of the invention, in a mixture of volatile linear alkanes, the volatile linear alkane having the smallest carbon number is predominant in the mixture.

According to another mode of the invention, use is made of a mixture of volatile linear alkanes in which the volatile linear alkane having the highest carbon number is predominant in the mixture.

By way of examples of mixtures suitable for the invention, mention may especially be made of the following mixtures:
from 50 to 90% by weight, preferably from 55 to 80% by weight, more preferably from 60 to 75% by weight of $C_n$ volatile linear alkane with n ranging from 7 to 14;
from 10 to 50% by weight, preferably from 20 to 45% by weight, preferably from 24 to 40% by weight of $C_{n+x}$ volatile linear alkane with x greater than or equal to 1, preferably x=1 or x=2, with n+x between 8 and 14, relative to the total weight of alkanes in said mixture.

In particular, said mixture of alkanes according to the invention contains:
less than 2% by weight, preferably less than 1% by weight, of branched hydrocarbons;
and/or less than 2% by weight, preferably less than 1% by weight, of aromatic hydrocarbons;
and/or less than 2% by weight, preferably less than 1% by weight and preferentially less than 0.1% by weight of unsaturated hydrocarbons in the mixture.

More particularly, a volatile linear alkane suitable for the invention may be used in the form of an n-undecane/n-tridecane mixture.

In particular, use will be made of a mixture of volatile linear alkanes comprising:
from 55 to 80% by weight, preferably from 60 to 75% by weight, of $C_{11}$ (n-undecane) volatile linear alkane;
from 20 to 45% by weight, preferably from 24 to 40% by weight, of $C_{13}$ (n-tridecane) volatile linear alkane relative to the total weight of alkanes in said mixture.

According to one particular embodiment, the mixture of alkanes is an n-undecane/n-tridecane mixture. In particular, such a mixture may be obtained according to Example 1 or Example 2 of WO 2008/155059.

According to another particular embodiment, use is made of the n-dodecane sold under the reference PARAFOL 12-97 by Sasol.

According to another particular embodiment, use is made of the n-tetradecane sold under the reference PARAFOL 14-97 by Sasol.

According to yet another embodiment, use is made of a mixture of n-dodecane and of n-tetradecane.

The composition of the invention may comprise from 5% to 50% by weight of volatile linear alkane(s), in particular from 5 to 40% by weight of volatile linear alkane(s), and more particularly from 5 to 30% of volatile linear alkane(s) relative to the total weight of the composition.

The volatile solvent is generally present in the composition of the present invention in an amount ranging from about 0% to about 95% by weight; such as from about 1% to about 60% by weight; such as from about 3% to about 10% by weight, based on the total weight of the composition.

Optional Ingredients

Tactile Modifier

The composition of the present invention may also contain at least one tactile modifier. Suitable tactile modifiers include, but are not limited to nylon, silica, and mixtures thereof.

Colorants

The composition of the present invention may also contain at least one colorant. Preferably, such colored compositions can be cosmetic compositions such as, for example, lip compositions (for example, lipstick or liquid lip colors or lip gloss), body tints, bronzers, self tanners, mascaras, eyeshadow, nail polish or foundations.

According to this embodiment, the at least one colorant is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and sub-ranges there between.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present the pigment is generally present in the composition of the present invention in an amount ranging from about 0% to about 15% by weight; such as from about 0.01% to about 10% by weight; such as from about 0.1% to about 5% by weight, all weights being based on the weight of the composition as a whole.

Organic Sunscreen Active

The composition of the present invention may also contain at least one organic sunscreen agent. Suitable chemical absorbers include, but are not limited to, p-aminobenzoic acid derivatives; anthranilates; benzophenones; camphor derivatives; benzylidene camphor derivatives (such as those sold under the trade name Mexoryl by L'Oréal); cinnamic derivatives; dibenzoyl methanes (such as avobenzone also known as Parsol® 1789); diphenylacrylate derivatives; salicylic derivatives; triazine derivatives; ethylhexyl triazone (such as that sold under the trade name Uvinul T 150 by BASF); diethylhexyl butamido triazone (such as that sold under the trade name Uvasorb HEB by 3V Sigma); bis-ethylhexyloxyphenol methoxyphenyl triazine (such as bemotrizinol sold under the trade name Tinosorb S by BASF); diethylamino hydroxybenzoyl hexyl benzoate (such as that sold under the trade name Uvinul A plus); benzimidazole compounds; bis-benzoazolyl derivatives; methylene bis-(hydroxyphenylbenzotriazole) compounds; the sunscreen polymers and silicones; and mixtures thereof. Exact amounts of the organic sunscreen agents will vary depending upon the sunscreen or sunscreens chosen and the desired Sun Protection Factor (SPF).

Active Agents

The composition of the present invention may also contain at least one active agent capable of imparting a benefit onto skin. It is to be understood that the active agents useful herein can in some instances provide more than one benefit or operate via more than one mode of action. Therefore, classifications herein are made for the sake of convenience and are not intended to limit the active to that particular application or applications listed.

For example, the compositions of the present invention may contain a safe and therapeutically effective amount of one or more pharmaceutically or cosmetically acceptable anti-acne active agents. Suitable anti-acne actives include, but are not limited to, resorcinol; sulfur; salicylic acid and salicylates; alpha-hydroxy acids; nonsteroidal anti-inflammatory agents; benzoyl peroxide; retinoic acid, isoretinoic acid and other retinoid compounds; adapalene; tazarotene; azelaic acid and azelaic acid derivatives; antibiotic agents, such as erythromycin and clyndamycin; zinc salts and complexes; and mixtures thereof.

For example, the compositions of the present invention may contain a safe and effective amount of one or more anti-wrinkle active agents. Suitable anti-wrinkle active agents for use in the compositions of the present invention include, but are not limited to, sulfur-containing D and L amino acids and their derivatives and salts, particularly the N-acetyl derivatives; thiols; hydroxy acids (e.g., alpha-hydroxy acids such as lactic acid and glycolic acid and their derivatives and salts; or beta-hydroxy acids such as salicylic acid and salicylic acid salts and derivatives), urea, hyaluronic acid, phytic acid, lipoic acid; lysophosphatidic acid, skin peel agents (e.g., phenol, resorcinol and the like), vitamin B3 compounds (e.g., niacinamide, nicotinic acid and nicotinic acid salts and esters, including non-vasodilating esters of nicotinic acid (such as tocopheryl nicotinate), nicotinyl amino acids, nicotinyl alcohol esters of carboxylic acids, nicotinic acid N-oxide and niacinamide N-oxide), vitamin B5 and retinoids (e.g., retinol, retinal, retinoic acid, retinyl acetate, retinyl palmitate, retinyl ascorbate).

The compositions of the present invention may contain a safe and effective amount of one or more anti-oxidant/radical scavengers. Suitable anti-oxidants/radical scavengers include, but are not limited to, ascorbic acid (vitamin C) and its salts; ascorbyl esters of fatty acids; ascorbic acid derivatives (e.g., magnesium ascorbyl phosphate, sodium ascorbyl phosphate, ascorbyl sorbate); tocopherol (vitamin E); tocopherol sorbate; tocopherol acetate; other esters of tocopherol; butylated hydroxy benzoic acids and their salts; 6-hydroxy-2,5,7,8-tetramethylchroman-2-carboxylic acid (commercially available under the tradename Trolox®); gallic acid and its alkyl esters, especially propyl gallate; uric acid and its salts and alkyl esters; sorbic acid and its salts; lipoic acid; amines (e.g., N,N-diethylhydroxylamine, amino-guanidine); sulfhydryl compounds (e.g., glutathione); dihydroxy fumaric acid and its salts; lysine pidolate; arginine pidolate; nordihydroguaiaretic acid; bioflavonoids; curcumin; lysine; methionine; proline; superoxide dismutase; silymarin; tea extracts; grape skin/seed extracts; melanin; rosemary extracts; artemia extract; diethylhexyl syringylidene malonate (such as that sold under the trade name Oxynex ST by Merck); senna alata; and their mixtures.

Among the active agents that may be mentioned are:
antipollution agents and/or free-radical scavengers;
depigmenting agents and/or propiymenting agents;
antiglycation agents;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
muscle relaxants;
tensioning agents;
desquamating agents;
moisturizers;
anti-inflammatory agents;
agents acting on the energy metabolism of cells;
insect repellants;
substance P or CGRP antagonists.

Emollients

The composition of the present invention may contain emollients. Suitable emollients include, but are not limited to, mineral oil; petrolatum; $C_7$-$C_{40}$ branched chain hydrocarbons; $C_1$-$C_{30}$ alcohol esters of $C_1$-$C_{30}$ carboxylic acids; $C_1$-$C_{30}$ alcohol esters of $C_2$-$C_{30}$ dicarboxylic acids; monoglycerides of $C_1$-$C_{30}$ carboxylic acids; diglycerides of $C_1$-$C_{30}$ carboxylic acids; triglycerides of $C_1$-$C_{30}$ carboxylic acids; ethylene glycol monoesters of $C_1$-$C_{30}$ carboxylic acids; ethylene glycol diesters of $C_1$-$C_{30}$ carboxylic acids; propylene glycol monoesters of $C_1$-$C_{30}$ carboxylic acids; propylene glycol diesters of $C_1$-$C_{30}$ carboxylic acids; $C_1$-$C_{30}$ carboxylic acid monoesters and polyesters of sugars, for example, sefa cottonate (sucrose polycottonseedate); polydialkylsiloxanes; polydiarylsiloxanes; polyalkarylsiloxanes; cyclomethicones having 3 to 9 silicon atoms; vegetable oils; hydrogenated vegetable oils; polypropylene glycol $C_4$-$C_{20}$ alkyl ethers; di $C_8$-$C_{30}$ alkyl ethers; and mixtures thereof.

Self-Tanning Active Agents

The composition of the present invention may also contain a self-tanning active agent. Suitable self tanning agents include, but are not limited to, monocarbonyl or polycarbonyl compounds, such as isatin, alloxan, ninhydrin, glyceraldehyde, mesotartaric aldehyde, glutaraldehyde, erythrulose and dihydroxyacetone (DHA).

Skin Lightening/Whitening Agents

The composition of the present invention may contain a skin lightening/whitening agent. Suitable skin lightening/whitening agents include, but are not limited to, hydroquinone; azelaic acid and other related dicarboxylic acids, and salts and derivatives thereof; retinoids; kojic acid; arbutin; nicotinic acid and its precursors, salts and derivatives; arbutin; ascorbic acid and salts and derivatives thereof (e.g., magnesium ascorbyl phosphate or sodium ascorbyl phosphate); herbal extracts (e.g., licorice extract, mulberry extract); and mixtures thereof.

Thickeners

Hydrophilic thickeners that may be mentioned include carboxyvinyl polymers such as the Carbopol products (carbomers) and the Pemulen products (acrylate/C10-C30-alkylacrylate copolymer); polyacrylamides, for instance the crosslinked copolymers sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, which are optionally crosslinked and/or neutralized, for instance the poly(2-acrylamido-2-methylpropanesulfonic acid) sold by the company Hoechst under the trade name "Hostacerin AMPS" (CTFA name: ammonium polyacryldimethyltauramide); cellulose-based derivatives such as hydroxyethylcellulose; polysaccharides and especially gums such as xanthan gum; and mixtures thereof.

Needless to say, a person skilled in the art will take care to select the optional additional compound(s) mentioned above and/or the amounts thereof such that the advantageous properties intrinsically associated with the compositions in accordance with the invention are not, or are not substantially, adversely affected by the envisaged addition(s).

The compositions according to the invention find their application in a large number of treatments, especially cosmetic treatments, of the skin, the lips and the hair, including the scalp, especially for protecting and/or caring for the skin, the lips and/or the hair, and/or for making up the skin and/or the lips.

The present invention will be better understood from the examples that follow, all of which are intended for illustrative purposes only and are not meant to unduly limit the scope of the invention in any way.

EXAMPLES

The present invention is further described in terms of the following non-limiting examples. Unless otherwise indicated, all parts and percentages are on a weight-by-weight percentage basis.

Inventive Example 1

Lotion

| Raw Material | % w/w |
| --- | --- |
| Water | 26.8 |
| Humectant | 5 |
| Preservative | 0.7 |
| Salt | 1.9 |
| Emusifier | 6 |
| Solvent | 24.31 |
| Zinc Oxide | 9.75 |
| Silicone | 10.25 |
| Tactile Modifier | 2 |
| Talc | 2.5 |
| Titanium Dioxide | 7.8 |
| Fatty Acids | 0.8 |
| Colorant | 0.8 |
| Clay | 0.3 |
| Vitamin | 1 |
| Peptizing Agent | 0.09 |

Invention Example 2

Lotion

| Raw Material | % w/w |
| --- | --- |
| Water | 28.8 |
| Preservative | 0.7 |
| Salt | 2.6 |
| Emusifier | 6 |
| Solvent | 32.24 |
| Silicone | 5 |
| Tactile Modifier | 5 |
| Talc | 4 |
| Titanium Dioxide | 11.7 |
| Fatty Acids | 1.2 |
| Colorant | 1.2 |
| Clay | 0.5 |
| Antioxidant | 1 |
| Peptizing Agent | 0.06 |

Examples 3 (Lotion in Accordance with the Present Invention) and 4 (Placebo/Comparative Lotion)

| Raw Material | Example 3 % w/w | Example 4 % w/w |
| --- | --- | --- |
| Water | 23.87 | 27.12 |
| Preservative | 1 | 1 |
| Salt | 1.73 | 1.73 |
| Emusifier | 6 | 6 |
| Solvent | 40.84 | 39.1 |
| Silicone | 2 | 2 |
| Tactile Modifier | 5.5 | 5.5 |
| Booster | 4 | 4 |
| Talc | 1.25 | 0 |
| Titanium Dioxide | 11.02 | 11.02 |
| Fatty Acids | 1.1 | 1.1 |
| Antioxidant | 0.28 | 0.28 |
| Colorant | 1.15 | 1.15 |
| Clay | 0.2 | 0 |
| Peptizing Agent | 0.06 | 0 |

The two sunscreen compositions were compared—Example 3 containing the combination of talc (solid form dispersing aid) with activated clay, and Example 4 differing in that it did not contain the talc or clay of the composition of Example 3. The SPF comparison and calculations were carried out using standard protocol of The European Cosmetic Toiletry and Perfumery Association (COLIPA) for in-vitro SPF testing. The in-vitro SPF comparison between Examples 3 and 4 is shown in FIG. 1.

Figure 1:
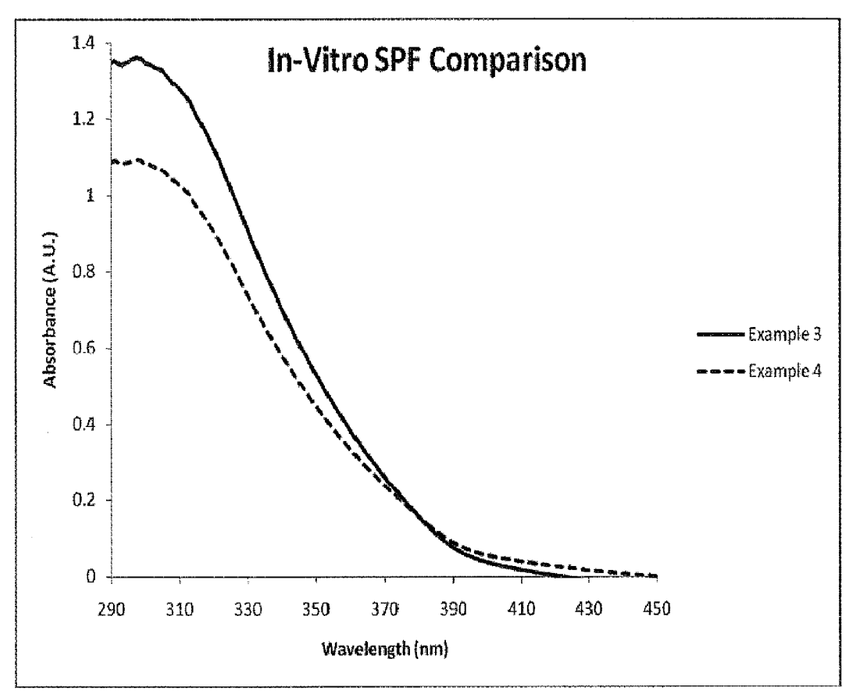
FIG. 1 is a bar graph evidencing the photo protection efficacy of a composition in accordance with the present invention versus a comparative composition.

FIG. 1 illustrates an In-Vitro SPF comparison of Examples 3 (lotion in accordance with the present invention) and 4 (placebo/comparative lotion).

As evidenced in FIG. 1, the in-vitro SPF results show that Example 3, the inventive composition containing talc (solid form dispersing aid) and clay (activated), has a significantly greater absorbance through wavelength (nm) range of about 290 nm through about 390 nm, as compared to Example 4 which does not contain either an activated clay or solid form dispersing aid, evidencing that the synergistic sun protection (SPF) efficacy realized by the claimed invention.

What is claimed is:
1. A mineral sunscreen composition comprising:
   (a) 0.2% by weight, based on the total weight of the composition, of at least one oil phase thickening agent chosen from an activated clay;
   (b) about 1.25% by weight, based on the total weight of the composition, of at least one substantially solid form dispersing aid;
   (c) at least one non-volatile solvent;
   (d) about 5% to about 15% by weight, based on the total weight of the composition, of at least one inorganic sunscreen active;
   (e) at least one emulsifier;
   (f) at least one volatile solvent; and
   (g) water,
   wherein (a) and (b) are present in the composition in a ratio by weight of about 1:6.25.
2. The composition of claim 1, wherein (a) is chosen from bentonite clay, hectorite clay, and montmorillonite clay.
3. The composition of claim 1, wherein (a) is a disteardimonium hectorite clay modified by propylene carbonate.
4. The composition of claim 1, wherein (a) is present in an amount of from about 0.01% to about 7.5% by weight, based on the total weight of the composition.

5. The composition of claim 1, wherein (a) is present in an amount of from about 0.1% to about 1.25% by weight, based on the total weight of the composition.

6. The composition of claim 1, wherein (b) is chosen from lauroyl lysine, mica, sericite, talc, polytetrafluoroethylene (PTFE), boron nitride, kaolin, oxychloride bismuth, titanium dioxide, aluminum oxide, silicon, perlite, oxychloride bismuth, barium sulfate, glass particles, zinc oxide, mica-barium sulfate, and synthetic mica.

7. The composition of claim 1, wherein (b) is talc.

8. The composition of claim 1, wherein (b) is present in an amount of from about 0.1% to about 30% by weight, based on the total weight of the composition.

9. The composition of claim 1, wherein (b) is present in an amount of from about 1% to about 5% by weight, based on the total weight of the composition.

10. The composition of claim 1, wherein (c) is chosen silicone oils, hydrocarbon oils and mixtures thereof.

11. The composition of claim 1, wherein (c) is present in an amount of from about 5% to about 80% by weight, based on the total weight of the composition.

12. The composition of claim 1, wherein (d) is chosen from cerium oxides, chromium oxides, cobalt oxides, iron oxides, red petrolatum, silicone-treated titanium dioxide, titanium dioxide, zinc oxide, zirconium oxide, and mixtures thereof.

13. The composition of claim 1, wherein (d) is present in an amount of from about 0.1% to about 50% by weight, based on the total weight of the composition.

14. The composition of claim 1, wherein (d) is present in an amount of from about 5% to about 15% by weight, based on the total weight of the composition.

15. The composition of claim 1, wherein (e) is present in an amount of from about 0% to about 15% by weight, based on the total weight of the composition.

16. The composition of claim 1, wherein (f) is present in an amount of from about 0% to about 95% by weight, based on the total weight of the composition.

17. The composition of claim 1 further comprising at least one tactile modifier.

18. The composition of claim 17 wherein the tactile modifier is chosen from nylon and/or silica.

19. The composition of claim 1 wherein (a) and (b) are present in the composition in a ratio by weight ranging from greater than or equal to 1:5 up to less than or equal to 1:9.

20. The composition of claim 1 further comprising at least one colorant.

21. A mineral sunscreen composition comprising:
   (a) about 0.2% by weight of at least one oil phase thickening agent chosen from an activated clay selected from the group consisting of disteardimonium hectorite, stearalkonium hectorite, quatemium-18 bentonite, quatemium-18 hectorite, and benzalkonium bentonite;
   (b) about 1.25% by weight of at least one substantially solid form dispersing aid comprising talc;
   (c) from about 30% to about 50% by weight of at least one non-volatile solvent;
   (d) from about 5% to about 15% by weight of at least one inorganic sunscreen active;
   (e) from about 1% to about 8% by weight of at least one emulsifier;
   (f) from about 3% to about 10% by weight of at least one volatile solvent; and
   (g) remainder by weight water,
   wherein the weights of (a)-(g) are based on the total weight of the composition; and
   wherein (a) and (b) are present in the composition in a ratio by weight of about 1:6.25.

22. A method tier protecting a keratinous substrate from harmful UV rays by topically applying onto the substrate a mineral sunscreen composition containing:
   (a) about 0.2% by weight, based on the total weight of the composition, of at least one oil phase thickening agent chosen from an activated clay;
   (b) about 1.25% by weight, based the total weight of the composition, of at least one substantially solid form dispersing aid;
   (c) at least one non-volatile solvent;
   (d) about 5% to about 15% by weight, based on the total weight of the composition, of at least one inorganic sunscreen active;
   (e) at least one emulsifier;
   (f) at least one volatile solvent; and
   (g) water,
   wherein (a) and (b) are present in the composition in a ratio by weight of about 1:6.25.

* * * * *